(12) United States Patent
Fu et al.

(10) Patent No.: US 7,684,647 B2
(45) Date of Patent: Mar. 23, 2010

(54) RIGID BODY TRACKING FOR RADIOSURGERY

(75) Inventors: Dongshan Fu, Santa Clara, CA (US); Gopinath Kuduvalli, San Jose, CA (US)

(73) Assignee: Accuray Incorporated, Sunnyvale, CA (US)

( * ) Notice: Subject to any disclaimer, the term of this patent is extended or adjusted under 35 U.S.C. 154(b) by 815 days.

(21) Appl. No.: 11/281,055

(22) Filed: Nov. 16, 2005

(65) Prior Publication Data

US 2007/0110289 A1 May 17, 2007

(51) Int. Cl.
*G06K 9/32* (2006.01)
(52) U.S. Cl. .................. 382/294; 345/630; 348/580; 708/442
(58) Field of Classification Search .............. 382/128, 382/100, 130, 131, 132, 154, 294; 345/619–689; 348/580; 708/442
See application file for complete search history.

(56) References Cited

U.S. PATENT DOCUMENTS

| | | | |
|---|---|---|---|
| 5,117,829 A | 6/1992 | Miller et al. | |
| 5,901,199 A * | 5/1999 | Murphy et al. | 378/65 |
| 5,954,647 A | 9/1999 | Bova et al. | |
| 6,235,038 B1 | 5/2001 | Hunter et al. | |
| 6,307,914 B1 | 10/2001 | Kunieda et al. | |
| 6,470,207 B1 | 10/2002 | Simon et al. | |
| 6,501,981 B1 | 12/2002 | Schweikard et al. | |
| 6,516,046 B1 | 2/2003 | Frohlich et al. | |
| 6,665,555 B2 | 12/2003 | Henderson et al. | |
| 6,782,287 B2 * | 8/2004 | Grzeszczuk et al. | 600/424 |
| 6,907,281 B2 * | 6/2005 | Grzeszczuk | 600/407 |
| 7,024,237 B1 | 4/2006 | Bova et al. | |
| 7,171,257 B2 * | 1/2007 | Thomson | 600/427 |
| 7,187,792 B2 | 3/2007 | Fu et al. | |
| 7,204,640 B2 * | 4/2007 | Fu et al. | 378/205 |
| 7,302,033 B2 * | 11/2007 | Carrano et al. | 378/41 |
| 7,327,865 B2 | 2/2008 | Fu et al. | |
| 7,480,399 B2 | 1/2009 | Fu et al. | |
| 2002/0077543 A1 | 6/2002 | Grzeszczuk et al. | |
| 2004/0092815 A1 | 5/2004 | Schweikard et al. | |
| 2004/0131150 A1 | 7/2004 | Pankratov et al. | |
| 2004/0267113 A1 * | 12/2004 | Thomson | 600/427 |
| 2005/0047544 A1 * | 3/2005 | Fu et al. | 378/63 |
| 2005/0049477 A1 | 3/2005 | Fu et al. | |
| 2005/0049478 A1 * | 3/2005 | Kuduvalli et al. | 600/407 |
| 2005/0249398 A1 * | 11/2005 | Khamene et al. | 382/154 |
| 2007/0003123 A1 * | 1/2007 | Fu et al. | 382/131 |
| 2007/0110289 A1 * | 5/2007 | Fu et al. | 382/128 |

OTHER PUBLICATIONS

Gustafsson, Adaptive Filtering and Change Detection, 2001, Wiley, ISBN: 9780471492870 Online ISBN: 9780470841617, p. 126.*

(Continued)

*Primary Examiner*—Anand Bhatnagar
(74) *Attorney, Agent, or Firm*—Blakely, Sokoloff, Taylor & Zafman LLP

(57) ABSTRACT

A method and apparatus compares in-treatment X-ray images of a volume with pre-treatment reference images of the volume and determines a combined similarity measure. A combined registration search space is searched to maximize the combined similarity measure and to jointly register the in-treatment X-ray images with the pre-treatment images.

25 Claims, 10 Drawing Sheets

OTHER PUBLICATIONS

Dongshan Fu et al., "Automated Skull Tracking for the CyberKnife Image-guided Radiosurgery System", Proceedings of SPIE on CD-ROM, Medical Imaging 2005, Feb. 12-17, 2005, San Diego, California, USA, vols. 5744-5750, Medical Imaging 2005: Visualization, Image-Guided Procedures, and Display, pp. 366-377.

G. P. Penney, J. Weese, "A comparison of similarity measures for use in 2D-3D medical image registration," IEEE Trans. Med. Imag., vol. 17, Aug. 1998, pp. 586-595.

Coste-Manière, E., "Robotic whole body stereotactic radiosurgery: clinical advantages of the CyberKnife® integrated system", The International Journal of Medical Robotics+Computer Assisted Surgery, 2005, www.roboticpublications.com, pp. 28-39.

International Report on Patentability, International Application No. PCT/US04/27158, International filing date Aug. 20, 2004, mailed Feb. 9, 2006, 10 pages.

International Search Report, International Application No. PCT/US04/27158, International filing date Aug. 20, 2004, mailed Sep. 6, 2005, 16 pages.

Maintz, J.B.A., et al., A survey of medical image registration, Medical Image Analysis, vol. 2, 1998, pp. 1-37.

McLaughlin, R., et al., "A comparison of intensity-based registration and feature-based registration for neurointerventions," in Lecture Notes in Computer Science, T. Dohi and R. Kikinis, Eds. Berlin, Germany. Springer-Verlag, 2002, vol. 2489, Proc. MICCAI'02, pp. 517-524.

Murphy, Martin J., "An automatic six-degree-of-freedom image registration algorithm for image-guided frameless sterotaxic radiosurgery," Med. Phys. 24(6), 857-866, Jun. 1997.

Penney, Graeme P., et al., "Validation of a two- to three-dimensional registration algorithm for aligning preoperative CT images and intraoperative fluoroscopy images," Med. Phys. 28(6), 1024-1032.

Sarrut, D., et al, "Patient positioning in radiotherapy by registration of 2D portal to 3D CT images by a contend-based research with similarity measures," CARS 2000, 707-712.

Weese, J., et al., "Fast Voxel-Based 2D/3D Registration Using A Volume Rendering Method Based On Sharp-Warp Factorization" in SPIE Medical Imaging 1999: Image Processing, 1999, pp. 802-810.

* cited by examiner

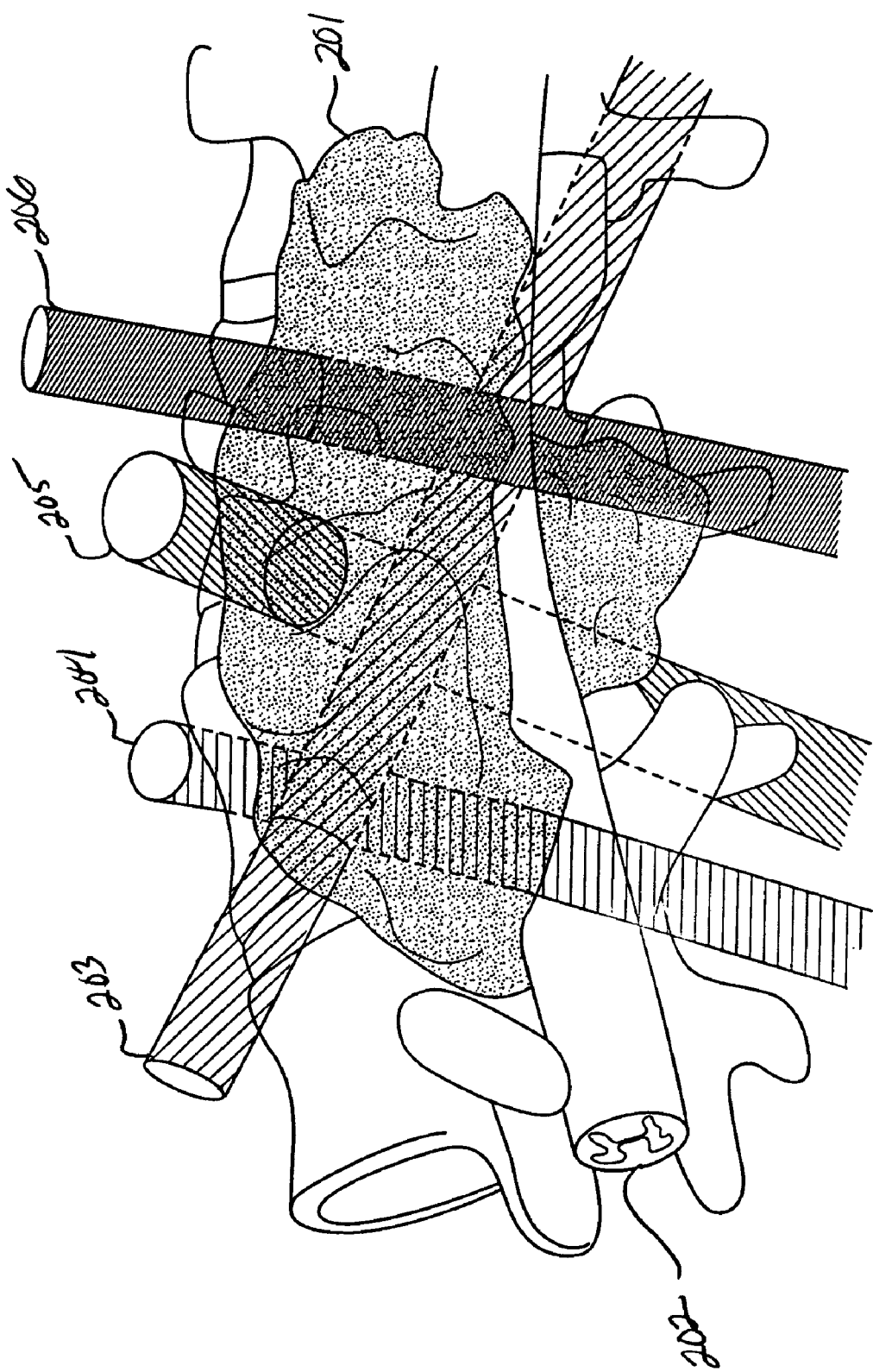

US 7,684,647 B2

RIGID BODY TRACKING FOR RADIOSURGERY

CROSS-REFERENCE TO RELATED APPLICATIONS

This application is related to U.S. patent application Ser. No. 10/652,786, titled "Apparatus and Method for Registering 2D Radiographic Images With Images Reconstructed From 3D Scan Data," filed Aug. 29, 2003. This application is also related to U.S. patent application Ser. No. 10/652,717, titled "Apparatus and Method for Determining Measure of Similarity Between Images," filed Aug. 29, 2003.

TECHNICAL FIELD

Embodiments of the invention relate to the field of medical imaging and, in particular, to the registration of medical images.

BACKGROUND

Radiosurgery and radiotherapy systems are radiation treatment systems that use external radiation beams to treat pathological anatomies (e.g., tumors, lesions, vascular malformations, nerve disorders, etc.) by delivering a prescribed dose of radiation (e.g., X-rays or gamma rays) to the pathological anatomy while minimizing radiation exposure to surrounding tissue and critical anatomical structures (e.g., the spinal chord). Both radiosurgery and radiotherapy are designed to necrotize the pathological anatomy while sparing healthy tissue and the critical structures. Radiotherapy is characterized by a low radiation dose per treatment, and many treatments (e.g., 30 to 45 days of treatment). Radiosurgery is characterized by a relatively high radiation dose in one, or at most a few, treatments.

In both radiotherapy and radiosurgery, the radiation dose is delivered to the site of the pathological anatomy from multiple angles. As the angle of each radiation beam is different, each beam can intersect a target region occupied by the pathological anatomy, while passing through different regions of healthy tissue on its way to and from the target region. As a result, the cumulative radiation dose in the target region is high and the average radiation dose to healthy tissue and critical structures is low. Radiotherapy and radiosurgery treatment systems can be classified as frame-based or image-guided.

In frame-based radiosurgery and radiotherapy, a rigid and invasive frame is fixed to the patient to immobilize the patient throughout a diagnostic imaging and treatment planning phase, and a subsequent treatment delivery phase. The frame is fixed on the patient during the entire process. Image-guided radiosurgery and radiotherapy (IGR) eliminate the need for invasive frame fixation by tracking and correcting for patient movement during treatment.

Image-guided radiotherapy and radiosurgery systems include gantry-based systems and robotic-based systems. In gantry-based systems, the radiation source is attached to a gantry that moves around a center of rotation (isocenter) in a single plane. Each time a radiation beam is delivered during treatment, the axis of the beam passes through the isocenter. In some gantry-based systems, known as intensity modulated radiation therapy (IMRT) systems, the cross-section of the beam is shaped to conform the beam to the pathological anatomy under treatment. In robotic-based systems, the radiation source is not constrained to a single plane of rotation. -

In image-guided systems, patient tracking during treatment is accomplished by registering two-dimensional (2-D) in-treatment X-ray images of the patient (indicating where the patient is) to 2-D reference projections of one or more pre-treatment three-dimensional (3-D) volume studies of the patient (indicating where the patient should be to match the treatment plan). The pre-treatment 3-D volume studies may be computed tomography (CT) scans, magnetic resonance imaging (MRI) scans, positron emission tomography (PET) scans or the like.

The reference projections (reference images), known as digitally reconstructed radiographs (DRRs) are generated using ray-tracing algorithms that replicate the geometry of the in-treatment X-ray imaging system to produce images that have the same scale as the in-treatment X-ray images. Typically, the in-treatment X-ray system is stereoscopic, producing images of the patient from two different points of view (e.g., orthogonal views).

The registration process compares the in-treatment X-ray images and the DRRs in each projection, and produces independent difference measures in each projection, which are sensitive to registration parameters such as rotational and translational misalignments. Each projection is characterized by its own search space where the registration parameters can be searched to minimize the associated difference measure for that projection. However, two of the registration parameters in one projection are coupled to the registration parameters in the other projection by the geometry of the X-ray imaging system. As a result, these two common registration parameters that are independently estimated in each projection may be not consistent . . . . Therefore, the registration process alternates between the two projections to maximize the overall registration, and the overall registration process may be slowed.

BRIEF DESCRIPTION OF THE DRAWINGS

The present invention is illustrated by way of example, and not by limitation, in the figures of the accompanying drawings in which:

FIG. 1B illustrates non-isocentric radiation treatment in one embodiment of an image-guided radiosurgery system;

DETAILED DESCRIPTION

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. The term "coupled" as used herein, may mean directly coupled or indirectly coupled through one or more intervening components or systems. The term "X-Ray image" as used herein may mean a visible X-ray image (e.g., displayed on a video screen) or a digital representation of an X-ray image (e.g., a file corresponding to the pixel output of an X-ray detector). The term "in-treatment image" as used herein may refer to images captured at any point in time during a treatment delivery phase of a radiosurgery or radiotherapy procedure, which may include times when the radiation source is either on or off. The term IGR as used herein may refer to image-guided radiotherapy, image-guided radiosurgery or both.

Unless stated otherwise as apparent from the following discussion, it will be appreciated that terms such as "processing," "computing," "determining," "estimating," "searching" or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage, transmission or display devices. Embodiments of the method described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

Figure 1A:
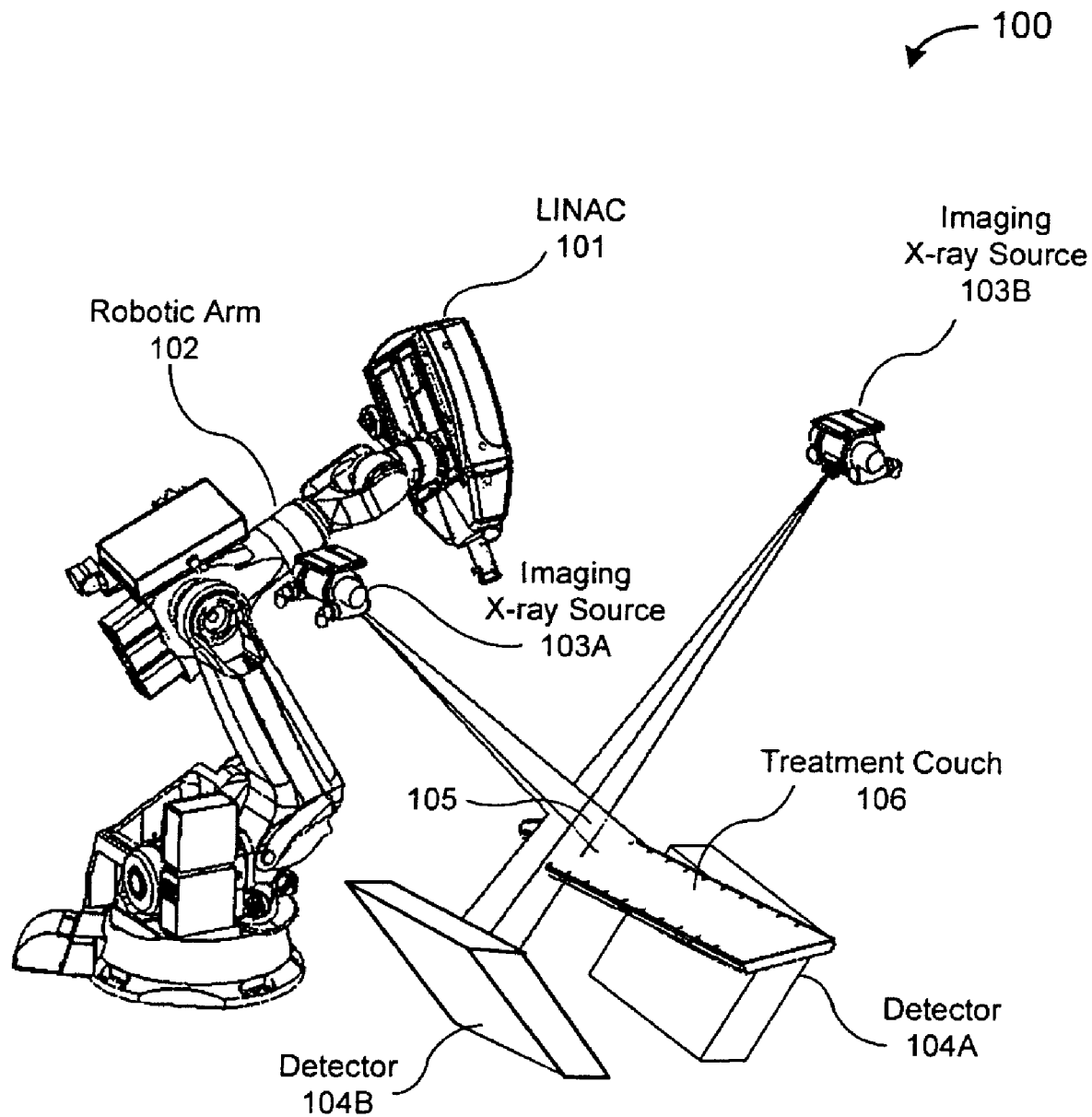
FIG. 1A illustrates an image-guided robotic radiosurgery system in one embodiment.

FIG. 1A illustrates the configuration of an image-guided, robotic-based radiation treatment system 100, such as the CyberKnife® Radiosurgery System manufactured by Accuray, Inc. of California. In FIG. 1A, the radiation treatment source is a linear accelerator (LINAC) 101 mounted on the end of a robotic arm 102 having multiple (e.g., 5 or more) degrees of freedom in order to position the LINAC 101 to irradiate a pathological anatomy (target region or volume) with beams delivered from many angles, in many planes, in an operating volume around the patient. Treatment may involve beam paths with a single isocenter, multiple isocenters, or with a non-isocentric approach. FIG. 1B illustrates non-isocentric radiation treatment in one embodiment. In FIG. 1B, a pathological anatomy (e.g., a tumor) 201 growing around a spinal cord (202) is treated for example, by radiation treatment beams 203, 204, 205 and 206, which each intersect the pathological target volume without converging on a single point, or isocenter, within the target).

In FIG. 1A, the imaging system may include X-ray sources 103A and 103B and X-ray detectors (imagers) 104A and 104B. The two x-ray sources 103A and 103B may be mounted in fixed positions on the ceiling of an operating room and may be aligned to project imaging x-ray beams from two different angular positions (e.g., separated by 90 degrees) to intersect at a machine isocenter 105 (which provides a reference point for positioning the patient on a treatment couch 106 during treatment) and to illuminate imaging planes of respective detectors 104A and 104B after passing through the patient. In other embodiments, system 100 may include more or less than two X-ray sources and more or less than two detectors, and any of the detectors may be movable rather than fixed. In yet other embodiments, the positions of the x-ray sources and the detectors may be interchanged.

The detectors 104A and 104B may be fabricated from a scintillating material that converts the X-rays to visible light (e.g., amorphous silicon), and an array of CMOS (complementary metal oxide silicon) or CCD (charge-coupled device) imaging cells that convert the light to a digital image that can be compared with the reference images during the registration process.

Figure 2A:
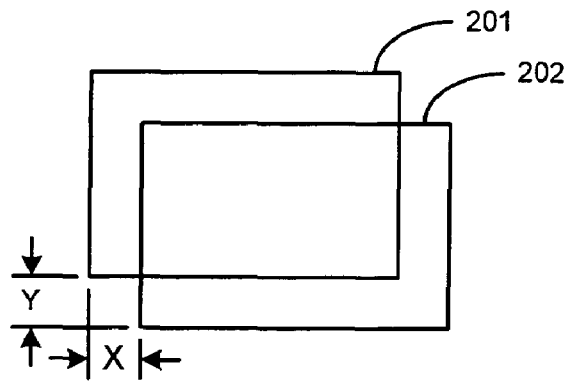
FIGS. 2A-2D illustrate examples of image misregistration.
Figure 2B:
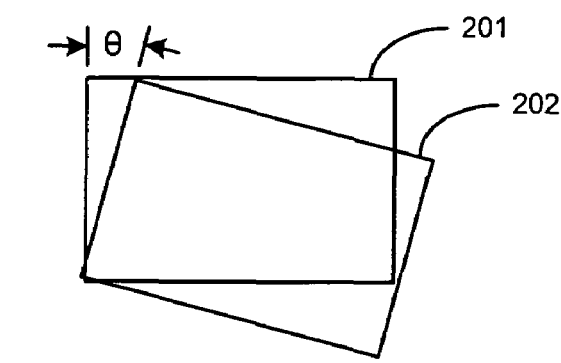
Figure 2C:
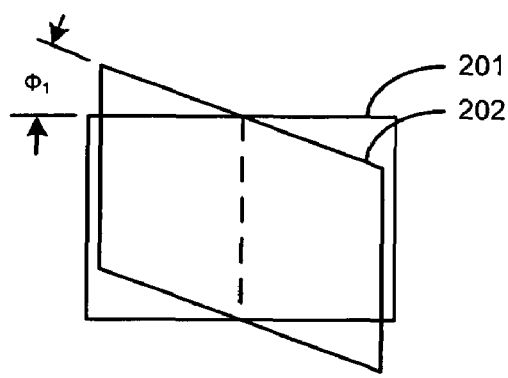
Figure 2D:
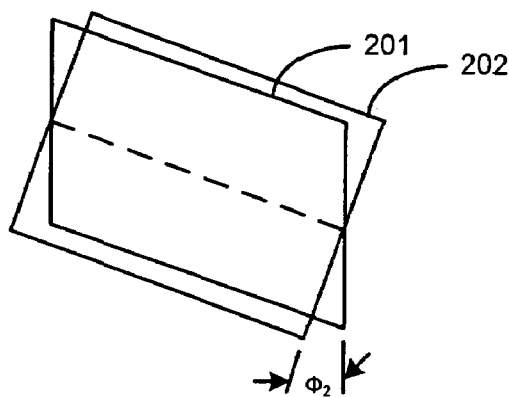

FIGS. 2A through 2D illustrate the ways in which two 2-D images 201 and 202 may be misaligned. FIG. 2A illustrates in-plane translation, which can be described in terms of linear displacement in two dimensions, x and y, between images 201 and 202. FIG. 2B illustrates in-plane rotation, which can be described in terms of a rotation, θ between image 201 and image 202. Together, FIGS. 2A and 2B define the dimensional space of in-plane transformations, which include x, y and θ. FIG. 2C illustrates a first type of out-of-plane rotation, which can be described in terms of an angular rotation, φ1, of image 202 with respect to one axis (e.g., a vertical axis) of image 201. FIG. 2D illustrates a second type of out-of-plane rotation, which can be described in terms of an angular rotation, φ2, of image 202 with respect to another axis (e.g., a horizontal axis) of image 201.

In the following descriptions of embodiments of the invention, CT scans may be used as an exemplary imaging modality for 3-D volume studies. Similarly, X-ray imaging may be used as an exemplary imaging modality for 2-D in-treatment imaging. Those skilled in the art will understand that other 3-D imaging modalities (e.g., MRI, PET, 3-D ultrasound) and other 2-D imaging modalities (e.g., fluoroscopy) may be used to equal effect in other embodiments.

Methods and apparatus are described for tracking patient movement during image-guided radiotherapy and/or radiosurgery by registering 2-D in-treatment X-ray images to pretreatment 3-D volume studies. In one embodiment, digitally reconstructed radiographs (DRR's) are generated offline from a 3-D volume study of the patient before treatment, and are used as reference images to register the patient's in-treatment position. Two stereoscopic in-treatment X-ray images of the patient are acquired, and a search space with six degrees of freedom is used, in a multi-step registration process, to maximize a combined similarity measure between the DRRs and the X-ray images in the two projections. The registration process produces a 3-D, 6 parameter rigid transformation between a patient coordinate system and an imaging coordinate system.

In general, medical image registration methods rely on the use of similarity measures to quantify differences between images, and on registration search algorithms to maximize the similarities (minimize the differences) between the images. One approach to image registration is based on extracting and matching image features (see, e.g., U.S. Pat. No. 5,901,199 by Murphy et al.). Image features may be anatomical edges, image gradients, contours, object surfaces, segmented objects or similar anatomical features. The image feature approach is computationally efficient because it uses only those portions of an image that contain recognizable features. However, because it uses less than the full image, its accuracy may be limited.

Another approach to image registration is based on image intensity that reflect variations in the density and radio-opacity of bone and tissue (see, e.g., G. P. Penney, J. Weese, "A comparison of similarity measures for use in 2D-3D medical image registration," *IEEE Trans. Med. Imag.*, vol. 17, pp.

586-595, August, 1998). The image intensity-based registration approach uses the entire image, and may yield greater accuracy, albeit at greater computational intensity. The computational intensity of either approach may be approximately proportional to the square of the number of parameters of the geometric search space used to register the images.

Image-guided radiosurgery systems (such as the CyberKnife® Radiosurgery System manufactured by Accuray, Inc. of California) require an automatic, accurate, fast and robust (e.g., tolerant of large initial errors) tracking method for frequent patient alignment and patient position correction. In order to meet these requirements, the tracking algorithm should leverage the following considerations. First, out-of-plane rotations are more difficult to estimate than in-plane translations and rotations, because the image variations in a 2-D plane due to out-of-plane rotations are subtle (e.g., small changes in out-of-plane rotations correspond to very small changes in the 2-D in-treatment X-ray images). Therefore, dependence on out-of-plane rotation parameters should be reduced or eliminated. Second, during initial patient alignment, the initial misregistration may be large. Therefore, automatic and fast detection of large initial displacements should be an integral part of the search method.

In one embodiment, an imaging system uses two stereoscopic projections. A set of DRRs corresponding to each projection is generated before treatment begins. The sets of DRRs may include different combinations of out-of-plane rotations, in closely spaced increments (e.g., one degree increments), corresponding to an expected range of in-treatment patient movements. A pair of nominal DRRs (e.g., zero degree out-of-plane rotations) is selected and compared with a corresponding pair of in-treatment X-ray images. A combined similarity measure, based on the comparisons in both projections, uses three in-plane translation parameters, two in-plane rotation parameters and one out-of-plane rotation parameter to define a 6-parameter registration search space. The search space may be searched in a multi-step process, using different search methods and different similarity measure methods, to maximize the combined similarity measure. The registration results may be converted directly to three translation parameters and three rotation parameters in a 3-D rigid transformation between a patient coordinate system and an imaging coordinate system.

Figure 3:
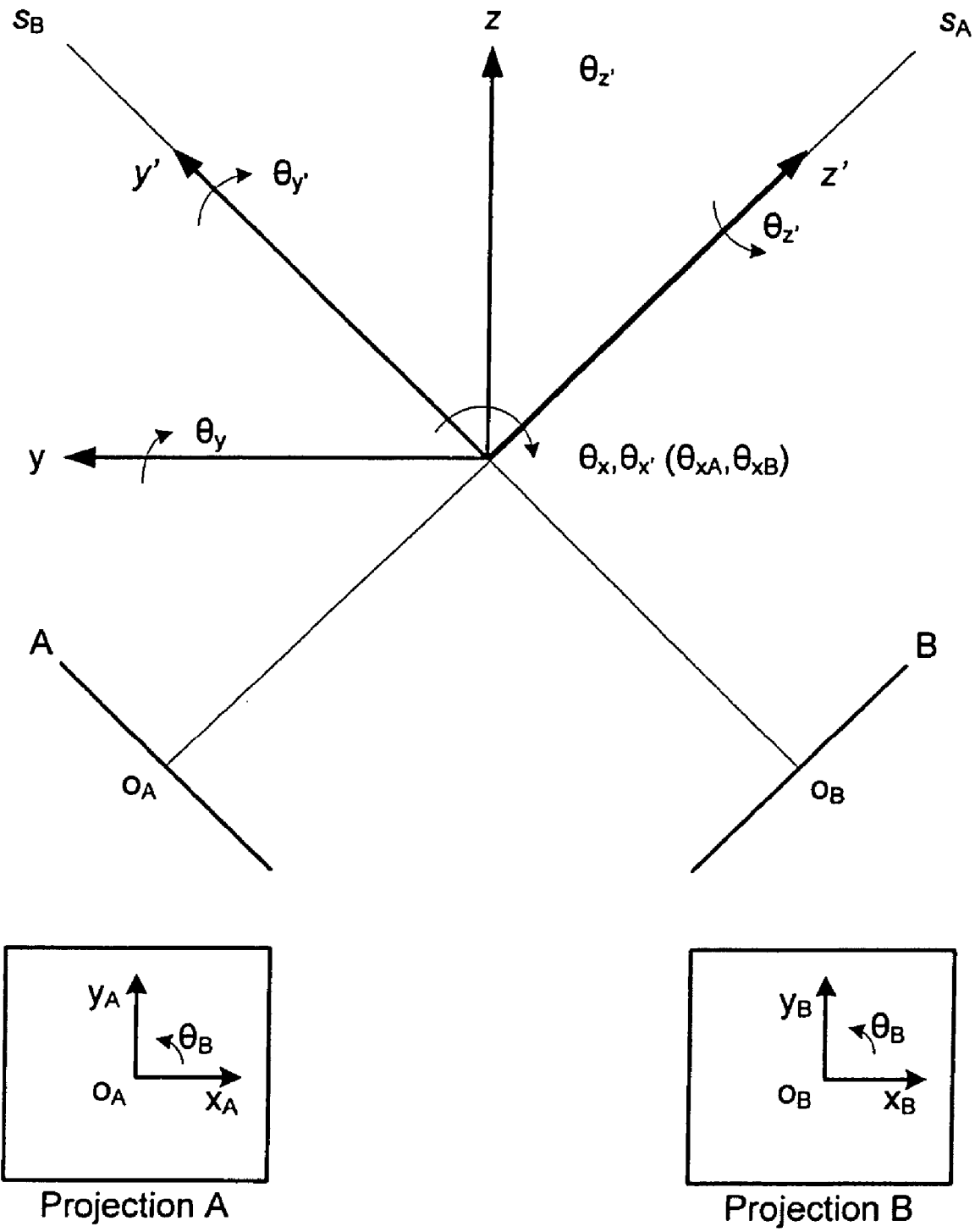
FIG. 3 illustrates a reference coordinate system in one embodiment of rigid body tracking.

For certain anatomical structures (e.g., the skull), a 3-D rigid transformation may be assumed for modeling patient movement. The 3-D rigid transformation may be described using six degrees of freedom: three translations and three rotations (roll, pitch and yaw) about three mutually orthogonal axes. Two orthogonal (or other pair of non-coaxial) X-ray projections may be used to solve these six parameters. FIG. 3 illustrates geometric relationships between a 3-D object (e.g., the patient) and the two 2-D X-ray projections in two X-ray detectors A and B, respectively. X-ray detectors A and B may obtain their X-ray projections from their respective X-ray sources, $s_A$ and $s_B$, which pass X-rays through the patient.

A 3-D coordinate system (xyz) may be defined for the patient, where the x-axis points inward into the page in FIG. 3. The patient position is represented by three translations and three rotations (x, y, z, $\theta_x$, $\theta_y$, $\theta_z$). The 2-D projections, projection A and projection B, are viewed from the directions $o_A s_A$ and $o_B s_B$, respectively. The direction of axis $x_A$ in the coordinates of projection A is opposite to that of axis x in the 3-D patient coordinates. The direction of axis $x_B$ in the coordinates of projection B is the same as that of axis x in the 3-D patient coordinates. In order to establish the relationship between the patient coordinate system and the two projection coordinate systems, another 3-D coordinate system (x'y'z') may be introduced, as shown in FIG. 3, where the 3-D rigid transformation is described by (x', y', z', $\theta_{x'}$, $\theta_{y'}$, $\theta_{z'}$). The relationships of the 3-D rigid transformation between the two coordinate systems may be expressed as $$x=x',\ y=(y'-z')/\sqrt{2},\ z=(y'+z')/\sqrt{2},$$

$$\theta_x=\theta_{x'},\ \theta_y=(\theta_{y'}-\theta_{z'})/\sqrt{2},\ \theta_z=(\theta_{y'}+\theta_{z'})/\sqrt{2}. \qquad (1)$$

In the 2-D coordinate system $(x_A y_A)$ for projection A, the 3-D rigid transformation may be decomposed into three in-plane transformation parameters $(x_A, y_A, \theta_A)$ and two out-of-plane rotation parameters $(\theta_{x_A}, \theta_{y'})$. Similarly, in the 2-D coordinate system $(x_B y_B)$ for projection B, the decomposition consists of the three in-plane transformation parameters $(x_B, y_B, \theta_B)$ and the two out-of-plane rotation parameters $(\theta_{x_B}, \theta_{z'})$. The number of parameters needed to define each projection independently may be reduced from five to four by noting that, $$\theta_{y'}=\theta_B, \qquad (2)$$

and that $$\theta_{z'}=\theta_A. \qquad (3)$$

Thus, the two projections may be completely defined by the two sets of four parameters $(x_A, y_A, \theta_A, \theta_{x_A})$ and $(x_B, y_B, \theta_B, \theta_{x_B})$. Similarity measures may be defined for each projection as functions of the respective parameters: $s_A=f(x_A, y_A, \theta_A, \theta_{x_A})$ and $S_B=f(x_B, y_B, \theta_B, \theta_{x_B})$. However, the total number of parameters needed to define the two projections jointly may be reduced to six by noting first that, $$\theta_{x_A}=\theta_{x_B}=\theta_x. \qquad (4)$$

Then, if $\alpha_A$ and $\alpha_B$ are geometric amplification factors (e.g., scale factors related to source-to-patient and patient-to-detector distances) for projections A and B, respectively, then the translations between the coordinate system (x'y'z') and the 2-D projection coordinate systems have the following relationships:

$$x'=-\alpha_A x_A=\alpha_B x_B,\ y'=\alpha_A y_A,\ z'=\alpha_B y_B \qquad (5)$$

Substituting the foregoing equivalences into equation set (1) yields:

$$x=-\alpha_A x_A=\alpha_B x_B,\ y=(\alpha_A y_A-\alpha_B i_B)/\sqrt{2},\ z=(\alpha_A y_A+\alpha_B y_B)/\sqrt{2},$$

$$\theta_x=\theta_{x_A}=\theta_{x_B},\ \theta_y=(\theta_B-\theta_A)/\sqrt{2},\ \theta_z=(\theta_B+\theta_A)/\sqrt{2}. \qquad (6)$$

Therefore, given a pair of DRRs and a pair of X-ray images in two projections, a combined similarity measure $S_{total}=S_A+S_B=f(x, y_A, y_B, \theta_x, \theta_A, \theta_B)$ may be globally maximized by searching in one six-parameter search space, rather than the two four-parameter search spaces required for independent registration in each projection. Subsequently, the registration results may be mapped to the patient coordinate system using equation set (6).

Figure 4:
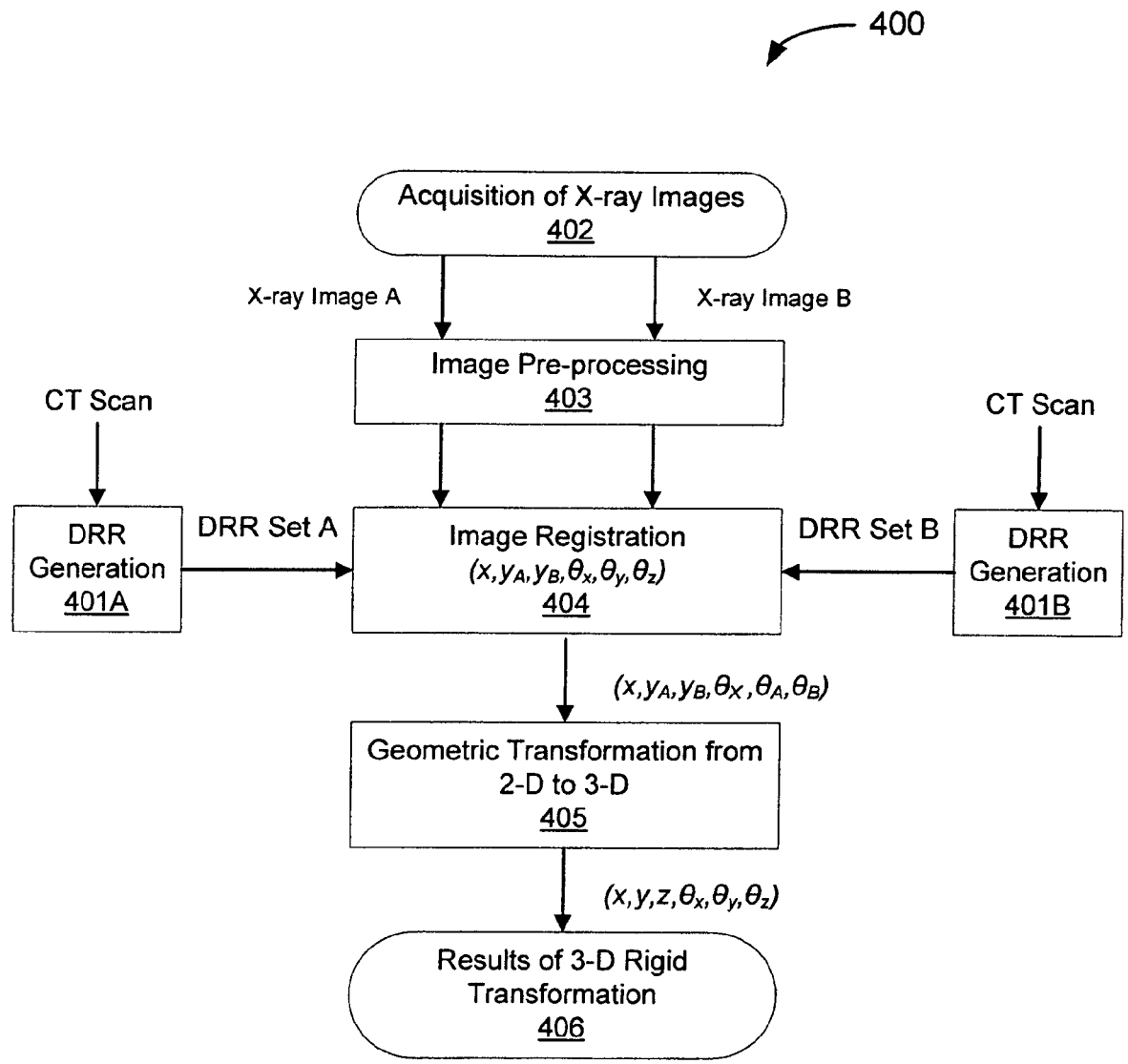
FIG. 4 is a flowchart illustrating a method in one embodiment of rigid body tracking.

FIG. 4 is a flowchart illustrating one embodiment of a method 400 for rigid body tracking. At step 401A, a set of reference DRR images is generated off-line for projection A. At step 401B, a set of reference DRR images is generated off-line for projection B. This process may be carried out after radiation treatment planning and before radiation treatment delivery. In the course of patient alignment and treatment, in-treatment X-ray images in projection A and projection B may be acquired (step 402) and pre-processed (step 403). In one embodiment, preprocessing may include matching scale, bit-depth, intensity or other image parameters as are known in the art. At step 404, the processed X-ray images in projections A and B are registered together with corresponding DRRs from the sets of DRRs, yielding the 6 transformation parameters (x, $y_A$, $y_B$, $\theta_x$, $\theta_A$, $\theta_B$) in the coordinate system of projection A and projection B. The 6 transformation parameters are then mapped to the patient coordinate system (x, y, z, $\theta_x$, $\theta_y$, $\theta_z$) in a 2-D to 3-D geometric transformation (step 405). At step 406, the registration result is applied to correct the patient position and/or the position of the radiation source (e.g., LINAC 101).

As described above, out-of-plane rotation parameters may be estimated from reference DRR images generated with predefined out-of-plane rotations, and in-plane transformation parameters may be computed directly from the 2-D in-treatment X-ray images. The registration method relies on the following observations: (1) detection of out-of-plane rotations is comparatively more difficult than detection of in-plane transformations. Hence, a more robust (i.e., error tolerant) similarity measure should be used for out-of-plane rotations, compared to in-plane transformations, for adequate accuracy; (2) The in-plane transformations may safely converge to an approximate solution by using a nominal reference (e.g., zero degree) DRR image, even when large out-of-plane rotations are present in the 3-D rigid transformation. It is also observed that the out-of-plane rotations may be detected with reasonably good accuracy using an in-plane transformation as an initial guess, which has already been roughly estimated using the equivalences between in-plane rotations and out-of-plane rotations in the two projections as described above; (3) a simple similarity measure (e.g., sum of squared differences described below) may be used during an initial search of the in-plane transformations, so that an initial estimate may be achieved in a short period of time.

Similarity measures compare an X-ray image with a DRR image to find the in-plane transformation parameters (translations and rotations) and the out-of-plane rotation parameters required to register the X-ray image with the DRR. Standardized pattern intensity difference and gradient difference similarity measures are similarity measures, known in the art, which are robust similarity measures. However, such methods may not be computationally efficient. In one embodiment, the present invention utilizes a pattern intensity similarity measure that is more computationally efficient than standard pattern intensity and is more accurate in determining out-of-plane rotations than gradient difference similarity measures.

Pattern intensity and gradient difference have the same mathematical meanings (see, e.g., G. P. Penney, J. Weese, "A comparison of similarity measures for use in 2D-3D medical image registration," *IEEE Trans. Med. Imag.*, vol. 17, pp. 586-595, August, 1998), but gradient difference is much more efficient in terms of computational cost than pattern intensity. Gradient difference formulations contains two terms, representing gradients in two mutually orthogonal directions (e.g., 0 degrees and 90 degrees). Pattern intensity has two additional terms, gradients bisecting the axes of the gradient difference formulation (e.g., 45 degrees and 135 degrees). A difference image between an X-ray image and a DRR image may be computed as:

$$I_{dif}(i,j) = I_{Xray}(i,j) - I_{DRR}(i,j). \quad (7)$$

where i and j are 2-D pixel coordinates in the respective X-ray and DRR images. A pattern intensity similarity measure based on the difference image may be expressed as an asymptotic function of the gradients of the difference image:

$$S_{PI} = \sum_{i,j} \sum_{k,l \subset R} \frac{\sigma^2}{\sigma^2 + (I_{dif}(i,j) - I_{dif}(i+k, j+l))^2}, \quad (8)$$

where σ is a weighting constant and R is a neighborhood using the pixel (i, j) as the center point.

Equation (8) for pattern intensity has several advantages. First, the difference image acts as a low-pass filter to effectively remove soft tissue while retaining high-frequency components corresponding to skeletal structures. This characteristic makes the algorithm robust to some amount of brightness intensity differential between X-ray and DRR images. Second, due to the asymptotic nature of the function, the measure is less sensitive to outlier pixels contaminated with random noise. Lastly, because the asymptotic function quickly approaches zero when its variable (for instance, ($I_{dif}(i,j) - I_{dif}(i+k, j+l)$) in equation (8) increases, large intensity differences such as image artifacts have the same effects on the similarity measure function regardless of their magnitude. As a result, pattern intensity similarity is less sensitive to image artifacts.

The sensitivity of the solution to variations of X-ray image may be minimized by careful selection of weighting constant σ. The stability of the results against X-ray image noise improves with an increased value of this constant. However, this choice is a tradeoff between stability and accuracy. When σ is too large, small image details may be obscured. In one embodiment, the value of σ may be selected to be in the range of 4 to 16.

The neighborhood R may be defined such that gradients in four directions are considered: horizontal, vertical, 45° diagonal and 135° diagonal. Based on this neighborhood, the pattern intensity may be expressed as $$S_{OPI} = \sum_{i,j} \frac{\sigma^2}{\sigma^2 + (I_{dif}(i,j) - I_{dif}(i, j-1))^2} + \quad (9)$$

$$\sum_{i,j} \frac{\sigma^2}{\sigma^2 + (I_{dif}(i,j) - I_{dif}(i-1, j))^2} +$$

$$\sum_{i,j} \frac{\sigma^2}{\sigma^2 + (I_{dif}(i,j) - I_{dif}(i-1, j-1))^2} +$$

$$\sum_{i,j} \frac{\sigma^2}{\sigma^2 + (I_{dif}(i,j) - I_{dif}(i-1, j+1))^2}.$$

Because the pattern intensity in equation (9) has two more terms than gradient difference, it includes more image information resulting in a more accurate registration for out-of-plane rotations.

The similarity measure in equation (9) is computationally intensive. To achieve a fast registration, a simple and efficient similarity measure may be used in an initial search stage. The sum of squared differences (SSD), is a simple similarity measure known in the art, and is commonly used in motion estimation for real-time video processing and also in intra-modality medical image registration. Its main advantage is reduced computation cost while retaining reasonably good accuracy. A closely related similarity measure known in the art, the sum of absolute differences (SAD), may also be used with similar advantages and disadvantages. As a result, SSD or SAD may be used in the initial search phases of a registration method to obtain approximate results. The pattern intensity similarity measure (9) described above may then be used to further refine the registration results.

Figure 5:
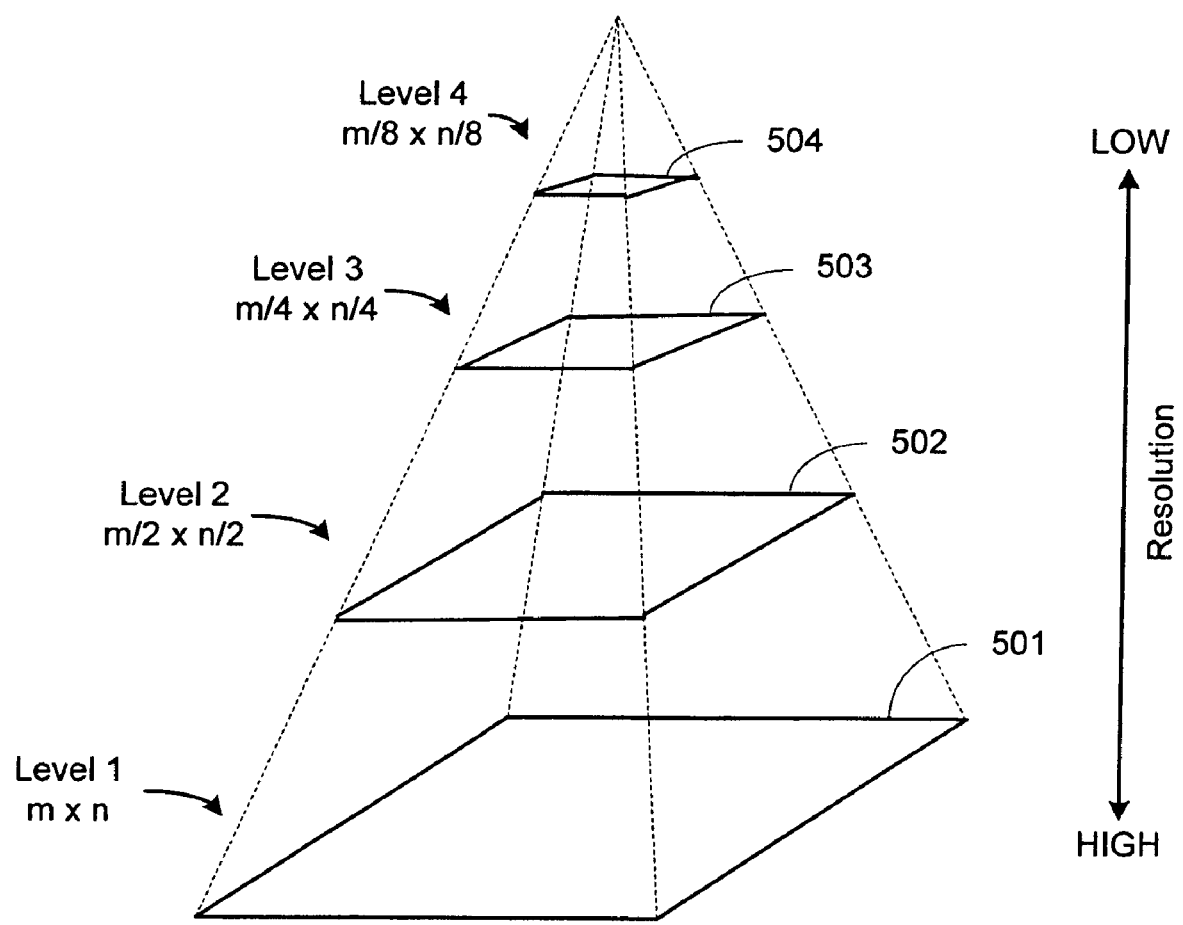
FIG. 5 illustrates multi-resolution matching in one embodiment of rigid body tracking.

Multi-resolution matching is a fast search method for estimating initial transformation (translation and/or rotation) parameters that may be refined in subsequent registration steps. With respect to the registration of an X-ray image to a DRR, each of the transformation parameters described above may be mapped to a 2-D image space representing the X-ray image under the transformation. FIG. 5 illustrates one embodiment of multi-resolution matching. As illustrated in FIG. 5, three image resolutions 502 (Level 2), 503 (Level 3) and 504 (Level 4) may be defined with respect to an original X-ray image 501 (Level 1), which may be used as the highest resolution image. Successively lower resolution images may be generated by sub-sampling pixels from the original X-ray image 501. In FIG. 5, resolution Level 1 is represented by the original X-ray image 501, which may contain m×n image pixels. A lower resolution image 502 is formed at Level 2 by selecting every other image pixel (sampling rate of ½) from the Level 1 image such that the Level 2 image contains m/2× n/2 image pixels. The sampling process may be repeated at Level 3 and Level 4 to produce image 503 with m/4×n/4 image pixels and image 504 with m/8×n/8 image pixels. In other embodiments, the number of resolution levels and/or the sampling rate may be different. As described below, multi-resolution matching may be applied to search for a number transformation parameters at once in a multi-parameter search space.

The basic idea of multi-resolution matching is to match the images at each level successively, starting with the lowest resolution. The results at the lower resolutions serve as rough estimates of the transformation parameter and reduce the risk of getting trapped in a local maximum of a similarity measure, as described below. The estimates at the lower resolution level are then passed to the next highest resolution level, where the parameters are refined using the higher resolution image space. In the final matching results, the accuracy depends on the spatial resolution of the highest resolution image space (e.g., image space 501).

Multi-resolution matching does not eliminate the risk that the similarity measure used at low resolution levels may converge to a local solution far away from a global optimum. In such a case, the result of further matching at subsequent higher resolution levels will most likely not converge to the global optimum. To overcome this risk, multiple candidates of estimates may be used. A sorted list of candidates with the best matches from the lower resolution level may be passed to the next highest resolution level. The candidates may be ranked by their SSD or SAD values, for example.

Gradient-based minimization search uses the first order derivatives of a similarity measure with respect to the search parameters (e.g., translations and/or rotations) to determine the directions that converge most rapidly toward a minimum difference (i.e., maximum similarity). Gradient-based minimization may be used during a parameter refinement stage of registration. If approximate results have already been calculated in the initial search steps, prior to refinement, the search ranges used for the search parameters are of much smaller magnitude. As a result, this phase may need only a few iterations to reach a stable solution.

A one parameter search may be used to determine an out-of-plane rotation because it may be calculated separately. In an initial out-of-plane rotation search, a rough rotation may be determined using the full range of reference DRR images sampled at every one-degree, for example. During refinement, a smaller search range centered at the previously estimated angle may be used to refine the reference. Then the final rotation may be calculated using, for example, a cubic spline interpolation or the like.

Sub-pixel matching is a search method that may be used to refine initial search results. The DRR images and the corresponding X-ray images are up-sampled by using linear interpolation. Then image matching is performing between the up-sampled DRR image and the corresponding up-sampled X-ray image to find the refined translations in sub-pixel accuracy.

Figure 6:
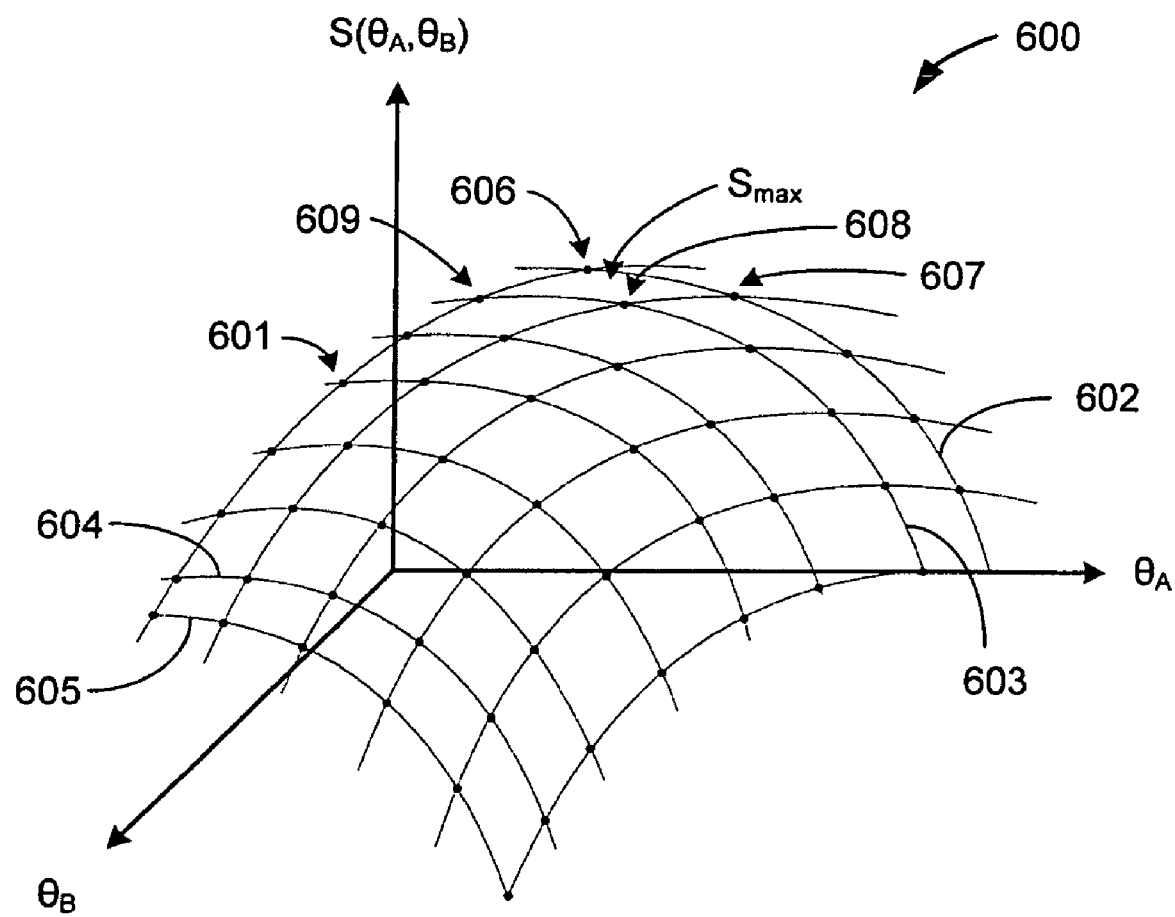
FIG. 6 illustrates curve-fitting in one embodiment of rigid body tracking.

Curve-fitting is a method for estimating a value of a function (e.g., a similarity measure) that is sampled at discrete values of the function's independent variables. FIG. 6 illustrates an example of curve fitting where a similarity measure S is sampled at discrete values of two parameters $\theta_A$ and $\theta_B$, for example. Each point (such as, for example point 601) on the surface 600 represents a discrete value of the similarity measure at particular discrete values of $\theta_A$ and $\theta_B$. In general, the maximum value of the similarity measure will not coincide with one of the discrete values. The maximum value of S (e.g., $S_{max}$) may be found by successive 2-D curve fitting (e.g., quadratic or cubic) to the data points. Curves such as curves 602, 603, 604 and 605 may be fitted to the discrete data points. $S_{max}$ may then be located by interpolating between points 606, 607, 608 and 609 on the fitted curves, for example.

Figure 7A:
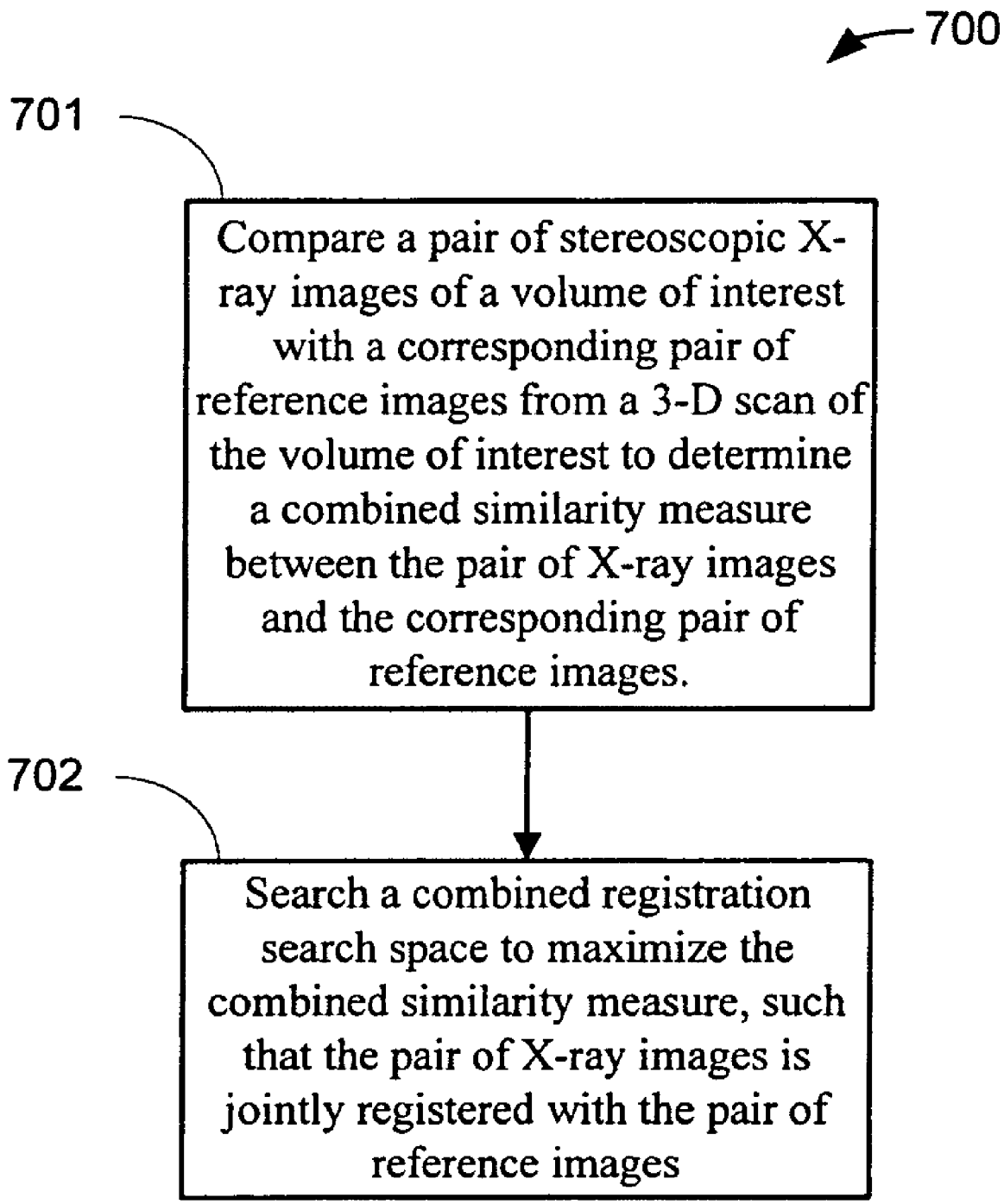
FIG. 7A is a flowchart illustrating a method for image registration in one embodiment of rigid body tracking.

Thus, in one embodiment, as illustrated in FIG. 7A, an image registration method 700 may include comparing a pair of stereoscopic X-ray images of a volume of interest with a corresponding pair of reference images from a 3-D scan of the volume of interest to determine a combined similarity measure between the pair of X-ray images and the corresponding pair of reference images (step 701). The method may also include searching a combined registration search space to maximize the combined similarity measure, such that the pair of X-ray images is jointly registered with the pair of reference images (step 702).

Figure 7B:
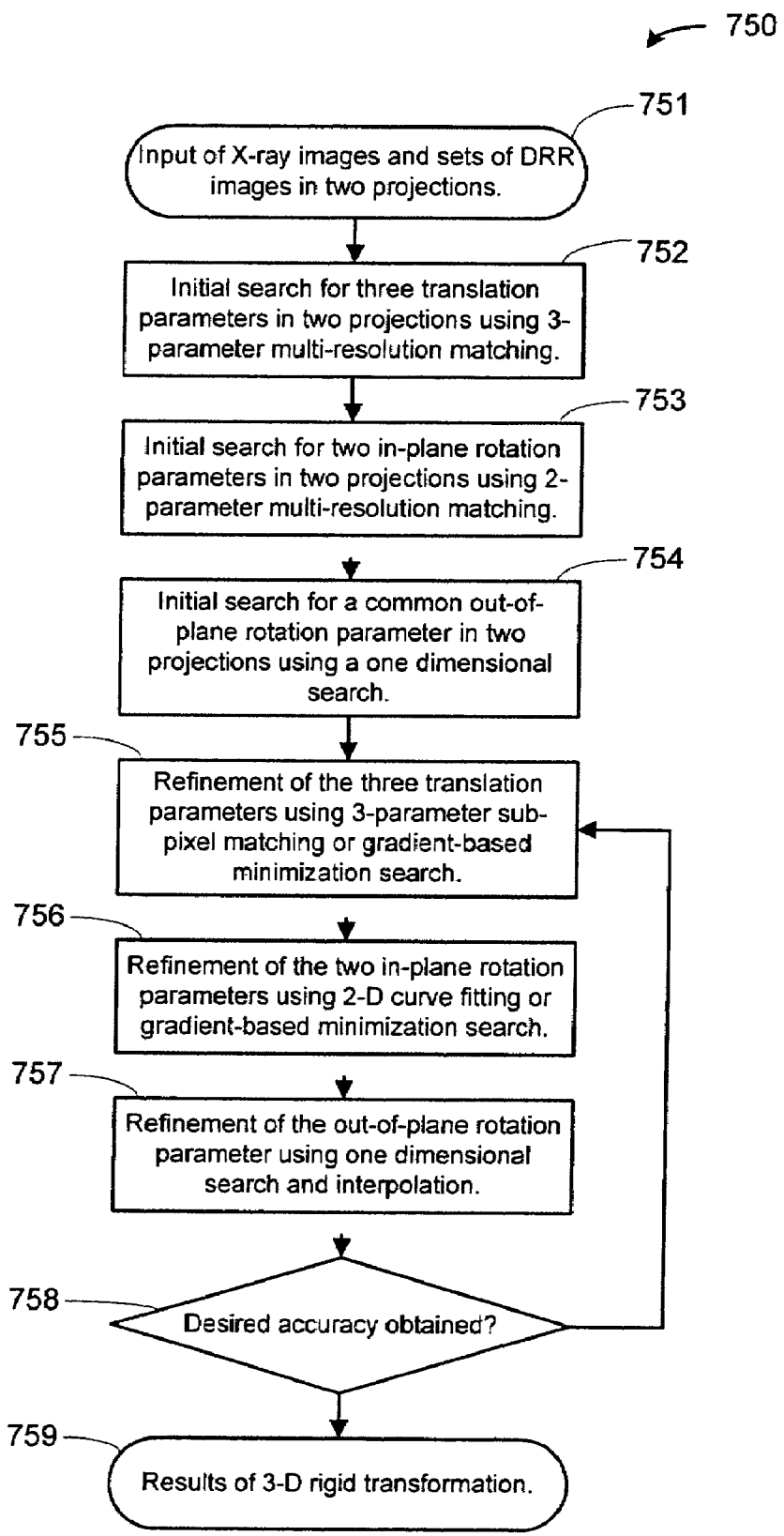
FIG. 7B is a flowchart illustrating another method for image registration in one embodiment of rigid body tracking.

In one embodiment, as illustrated in FIG. 7B, the image registration method of FIG. 7A may be implemented in a multi-step process 750. Different similarity measures and different search methods may be used at different steps in the registration process. In step 751, in-treatment X-ray images and corresponding sets of DRR images may be acquired and accessed, respectively, in two projections (e.g., projections A and B). In step 752, an initial search for the three translation parameters (x, $y_A$, $y_B$) in the two projections may be performed using 3-parameter multi-level matching as described above. In step 753, an initial search for the two in-plane rotation parameters ($\theta_A$, $\theta_B$) in the two projections may be performed using 2-parameter multi-level matching as described above. In step 754, an initial search for the one common out-of-plane rotation parameter ($\theta_x$) in the two projections may be implemented using a one parameter search method as described above. In step 755, the three translation parameters (x, $y_A$, $y_B$) may be refined using three parameter sub-pixel matching and/or a gradient-based minimization search as described above. In step 756, the two in-plane rotation parameters ($\theta_A$, $\theta_B$) may be refined using two parameter curve fitting and/or gradient-based minimization search described above. In step 757, the out-of-plane rotation parameter ($\theta_x$) may be refined using a one parameter search and interpolation method described above. At step 758, if a desired registration accuracy (e.g., ≦0.5 mm) has not been achieved, the refinement of the three translations at step 755, the two in-plane rotations at step 756, and the out-of-plane rotation at step 757 may be repeated. If, at step 758, the desired registration accuracy has been achieved, the search results from steps 755-757 may be applied in a 3-D (6 parameter) rigid transformation between the patient coordinate system (x, y, z, $\theta_x$, $\theta_y$, $\theta_z$) and the imaging coordinate system (x', y', z', $\theta_{x'}$, $\theta_{y'}$, $\theta_{z'}$) as described above (step 759).

Figure 8:
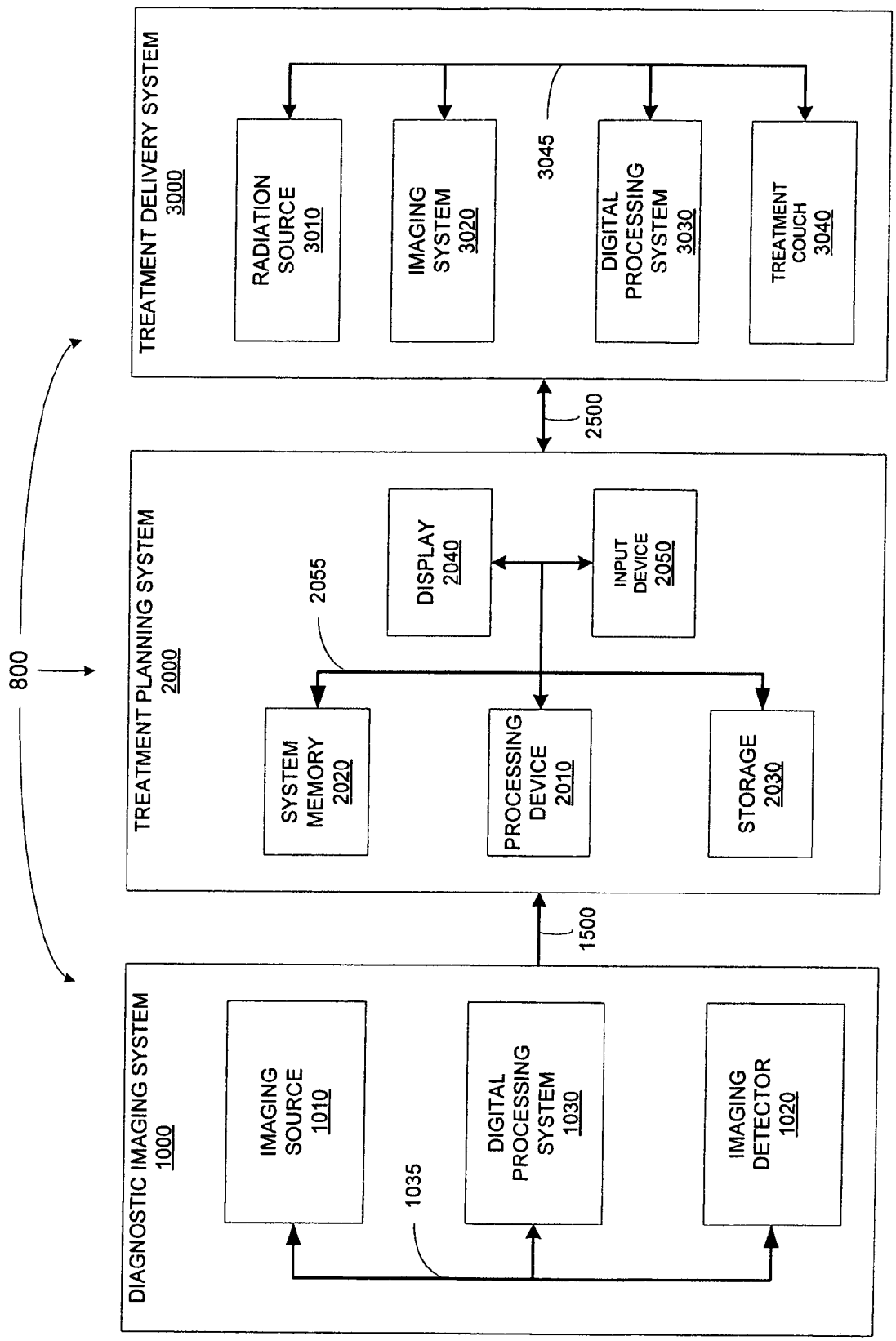
FIG. 8 illustrates a system in which embodiments of the present invention may be practiced.

FIG. 8 illustrates one embodiment of a system 800 that may be used in performing radiation treatment in which features of the present invention may be practiced. As described below and illustrated in FIG. 8, system 800 may include a diagnostic imaging system 1000, a treatment planning system 2000 and a treatment delivery system 3000.

Diagnostic imaging system 1000 may be any system capable of producing medical diagnostic images of a patient that may be used for subsequent medical diagnosis, treatment planning and/or treatment delivery. For example, diagnostic imaging system 1000 may be a computed tomography (CT) system, a magnetic resonance imaging (MRI) system, a positron emission tomography (PET) system, an ultrasound system or the like. For ease of discussion, diagnostic imaging system 1000 may be discussed below at times in relation to a CT x-ray imaging modality. However, other imaging modalities such as those above may also be used.

Diagnostic imaging system 1000 includes an imaging source 1010 to generate an imaging beam (e.g., x-rays, ultrasonic waves, radio frequency waves, etc.) and an imaging detector 1020 to detect and receive the beam generated by imaging source 1010, or a secondary beam or emission stimulated by the beam from the imaging source (e.g., in an MRI or PET scan).

The imaging source 1010 and the imaging detector 1020 may be coupled to a digital processing system 1030 to control the imaging operation and process image data. Diagnostic imaging system 1000 includes a bus or other means 1035 for transferring data and commands among digital processing system 1030, imaging source 1010 and imaging detector 1020. Digital processing system 1030 may include one or more general-purpose processors (e.g., a microprocessor), special purpose processor such as a digital signal processor (DSP) or other type of device such as a controller or field programmable gate array (FPGA). Digital processing system 1030 may also include other components (not shown) such as memory, storage devices, network adapters and the like. Digital processing system 1030 may be configured to generate digital diagnostic images in a standard format, such as the DICOM (Digital Imaging and Communications in Medicine) format, for example. In other embodiments, digital processing system 1030 may generate other standard or non-standard digital image formats. Digital processing system 1030 may transmit diagnostic image files (e.g., the aforementioned DICOM formatted files) to treatment planning system 2000 over a data link 1500, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 2000 includes a processing device 2010 to receive and process image data. Processing device 2010 may represent one or more general-purpose processors (e.g., a microprocessor), special purpose processor such as a digital signal processor (DSP) or other type of device such as a controller or field programmable gate array (FPGA). Processing device 2010 may be configured to execute instructions for performing treatment planning operations discussed herein.

Treatment planning system 2000 may also include system memory 2020 that may include a random access memory (RAM), or other dynamic storage devices, coupled to processing device 2010 by bus 2055, for storing information and instructions to be executed by processing device 2010. System memory 2020 also may be used for storing temporary variables or other intermediate information during execution of instructions by processing device 2010. System memory 2020 may also include a read only memory (ROM) and/or other static storage device coupled to bus 2055 for storing static information and instructions for processing device 2010.

Treatment planning system 2000 may also include storage device 2030, representing one or more storage devices (e.g., a magnetic disk drive or optical disk drive) coupled to bus 2055 for storing information and instructions. Storage device 2030 may be used for storing instructions for performing the treatment planning steps discussed herein.

Processing device 2010 may also be coupled to a display device 2040, such as a cathode ray tube (CRT) or liquid crystal display (LCD), for displaying information (e.g., a 2D or 3D representation of the VOI) to the user. An input device 2050, such as a keyboard, may be coupled to processing device 2010 for communicating information and/or command selections to processing device 2010. One or more other user input devices (e.g., a mouse, a trackball or cursor direction keys) may also be used to communicate directional information, to select commands for processing device 2010 and to control cursor movements on display 2040.

It will be appreciated that treatment planning system 2000 represents only one example of a treatment planning system, which may have many different configurations and architectures, which may include more components or fewer components than treatment planning system 2000 and which may be employed with the present invention. For example, some systems often have multiple buses, such as a peripheral bus, a dedicated cache bus, etc. The treatment planning system 2000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 2000 may share its database (e.g., data stored in storage device 2030) with a treatment delivery system, such as treatment delivery system 3000, so that it may not be necessary to export from the treatment planning system prior to treatment delivery. Treatment planning system 2000 may be linked to treatment delivery system 3000 via a data link 2500, which may be a direct link, a LAN link or a WAN link as discussed above with respect to data link 1500. It should be noted that when data links 1500 and 2500 are implemented as LAN or WAN connections, any of diagnostic imaging system 1000, treatment planning system 2000 and/or treatment delivery system 3000 may be in decentralized locations such that the systems may be physically remote from each other. Alternatively, any of diagnostic imaging system 1000, treatment planning system 2000 and/or treatment delivery system 3000 may be integrated with each other in one or more systems.

Treatment delivery system 3000 includes a therapeutic and/or surgical radiation source 3010 to administer a prescribed radiation dose to a target volume in conformance with a treatment plan. Treatment delivery system 3000 may also include an imaging system 3020 to capture intra-treatment images of a patient volume (including the target volume) for registration or correlation with the diagnostic images described above in order to position the patient with respect to the radiation source. Imaging system 3020 may include any of the imaging systems described above. Treatment delivery system 3000 may also include a digital processing system 3030 to control radiation source 3010, imaging system 3020 and a patient support device such as a treatment couch 3040. Digital processing system 3030 may be configured to register 2-D radiographic images from imaging system 3020, from two or more stereoscopic projections, with digitally reconstructed radiographs (DRRs) generated by digital processing system 1030 in diagnostic imaging system 1000 and/or DRRs generated by processing device 2010 in treatment planning system 2000. Digital processing system 3030 may include one or more general-purpose processors (e.g., a microprocessor), special purpose processor such as a digital signal processor (DSP) or other type of device such as a controller or field programmable gate array (FPGA). Digital processing system 3030 may also include other components (not shown) such as memory, storage devices, network adapters and the like. Digital processing system 3030 may be coupled to radiation source 3010, imaging system 3020 and treatment couch 3040 by a bus 3045 or other type of control and communication interface.

Digital processing system 3030 may implement methods (e.g., such as methods 400 and 700 described above) to register images obtained from imaging system 3020 with pre-operative treatment planning images in order to align the patient on the treatment couch 3040 within the treatment delivery system 3000, and to precisely position the radiation source with respect to the target volume.

The treatment couch 3040 may be coupled to another robotic arm (not illustrated) having multiple (e.g., 5 or more) degrees of freedom. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 3040 may be a component of another mechanical mechanism, such as the Axum® treatment couch developed by Accuray, Inc. of California, or be another type of conventional treatment table known to those of ordinary skill in the art.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of radiation beam(s).

It will be apparent from the foregoing description that aspects of the present invention may be embodied, at least in part, in software. That is, the techniques may be carried out in a computer system or other data processing system in response to its processor, such as processing device 2010, for example, executing sequences of instructions contained in a memory, such as system memory 2020, for example. In various embodiments, hardware circuitry may be used in combination with software instructions to implement the present invention. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by a processor or controller, such as processing device 2010.

A machine-readable medium can be used to store software and data which when executed by a data processing system causes the system to perform various methods of the present invention. This executable software and data may be stored in various places including, for example, system memory 2020 and storage 2030 or any other device that is capable of storing software programs and/or data.

Thus, a machine-readable medium includes any mechanism that provides (i.e., stores and/or transmits) information in a form accessible by a machine (e.g., a computer, network device, personal digital assistant, manufacturing tool, any device with a set of one or more processors, etc.). For example, a machine-readable medium includes recordable/non-recordable media (e.g., read only memory (ROM); random access memory (RAM); magnetic disk storage media; optical storage media; flash memory devices; etc.), as well as electrical, optical, acoustical or other forms of propagated signals (e.g., carrier waves, infrared signals, digital signals, etc.); etc.

It should be appreciated that references throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention. In addition, while the invention has been described in terms of several embodiments, those skilled in the art will recognize that the invention is not limited to the embodiments described. The embodiments of the invention can be practiced with modification and alteration within the scope of the appended claims. The specification and the drawings are thus to be regarded as illustrative instead of limiting on the invention.

What is claimed is:

1. A method comprising, using a processing device to perform:

comparing a pair of X-ray images of a volume of interest with a corresponding pair of reference images from a 3-D scan of the volume of interest to determine a combined similarity measure between the pair of X-ray images and the corresponding pair of reference images, wherein the combined similarity measure includes six transformation parameters; and searching a single combined six-parameter registration search space to maximize the combined similarity measure, wherein the pair of X-ray images is jointly registered with the pair of reference images.

2. The method of claim 1, wherein searching the combined registration search space comprises: searching for three in-plane translation parameters in two projections; searching for two in-plane rotation parameters in the two projections; and searching for a common out-of plane rotation parameter in the two projections.

3. The method of claim 1, wherein a first X-ray image of the pair of X-ray images is registered with a first reference image of the pair of reference images simultaneous to a second X-ray image of the pair of X-ray images being registered with a second reference image of the pair of reference images using a result of the search in the single combined six-parameter registration search space.

4. A method comprising, using a processing device to perform:
 comparing a pair of X-ray images of a volume of interest with a corresponding pair of reference images from a 3-D scan of the volume of interest to determine a combined similarity measure between the pair of X-ray images and the corresponding pair of reference images, wherein the combined similarity measure includes six transformation parameters; and
 searching a combined six-parameter registration search space to maximize the combined similarity measure, wherein the pair of X-ray images is jointly registered with the pair of reference images and wherein searching the combined six-parameter registration search space comprises:
  searching for no more than three in-plane translation parameters in two projections;
  searching for no more than two in-plane rotation parameters in the two projections, including searching initially for the two in-plane rotation parameters using two-parameter multi-resolution matching, and refining the two in-plane rotation parameters using one of 2-D curve-fitting and gradient minimization; and
  searching for no more than one common out-of-plane rotation parameter in the two projections.

5. The method of claim 4, wherein the combined registration search space comprises six transformation parameters, the method further comprising converting the six transformation parameters into a 3-D rigid transformation of the volume.

6. The method of claim 4, wherein searching for the three in-plane translation parameters in the two projections comprises: searching initially for the three in-plane translation parameters using three-parameter multi-resolution matching; and refining the three in-plane translation parameters using one of three-parameter sub-pixel matching and three-parameter gradient minimization.

7. The method of claim 4, wherein searching for the common out-of-plane rotation parameter in the two projections comprises: searching initially for the common out-of plane rotation parameter using a 1-D search method; and refining the common out-of plane rotation parameter using the 1-D search method and interpolation.

8. The method of claim 4, further comprising: determining whether the plurality of transformation parameters have enough accuracy to achieve a desired registration accuracy; and repeating the method of claim 3 if the plurality of transformation parameters do not have enough accuracy to achieve the desired registration accuracy; else applying the 3-D rigid transformation to the volume of interest.

9. An article of manufacture, including machine-accessible instructions that when accessed by a data processing system, cause the data processing system to perform a method, comprising:
 comparing a pair of X-ray images of a volume of interest with a corresponding pair of reference images of the volume of interest to determine a combined similarity measure between the pair of X-ray images and the corresponding reference images, wherein the combined similarity measure includes six transformation parameters; and
 searching a single combined six-parameter registration search space to maximize the combined similarity measure, wherein the pair of X-ray images is jointly registered with the pair of reference images.

10. The article of manufacture of claim 9, wherein searching the combined registration search space comprises: searching for three in-plane translation parameters in two projections; searching for two in-plane rotation parameters in the two projections; and searching for a common out-of-plane rotation parameter in the two projections.

11. An article of manufacture, including machine-accessible instructions that when accessed by a data processing system, cause the data processing system to perform a method, comprising:
 comparing a pair of X-ray images of a volume of interest with a corresponding pair of reference images of the volume of interest to determine a combined similarity measure between the pair of X-ray images and the corresponding reference images, wherein the combined similarity measure includes six transformation parameters; and
 searching a combined six-parameter registration search space to maximize the combined similarity measure, wherein the pair of X-ray images is jointly registered with the pair of reference images, and wherein searching the combined six-parameter registration search space comprises:
  searching for no more than three in-plane translation parameters in two projections;
  searching for no more than two in-plane rotation parameters in the two projections, wherein searching for the two in-plane rotation parameters in the two projections includes searching initially for the two in-plane rotation parameters using two-parameter multi-resolution matching, and refining the two in-plane rotation parameters using one of 2-D curve-fitting and gradient minimization; and
  searching for no more than one common out-of-plane rotation parameter in the two projections.

12. The article of manufacture of claim 11, wherein the combined registration search space comprises a plurality of transformation parameters, the method further comprising converting the plurality of transformation parameters into a 3-D rigid transformation of the volume.

13. The article of manufacture of claim 11, wherein searching for the three in-plane translation parameters in the two projections comprises: searching initially for the three in-plane translation parameters using three-parameter multi-resolution matching; and refining the three in-plane translation parameters using one of three-parameter sub-pixel matching and three-parameter gradient minimization.

14. The article of manufacture of claim 11, wherein searching for the common out-of-plane rotation parameter in the two projections comprises: searching initially for the common out-of-plane rotation parameter using a 1-D search method; and refining the common out-of-plane rotation parameter using the 1-D search method and interpolation.

15. The article of manufacture of claim 11, the method further comprising: determining whether the plurality of transformation parameters have enough accuracy to achieve a desired registration accuracy; and repeating the method of claim 10 if the plurality of transformation parameters do not have enough accuracy to achieve the desired registration accuracy; else applying the 3-D rigid transformation to the volume of interest.

16. A system comprising a processing device, wherein the processing device is configured to compare a pair of X-ray images of a volume of interest with a corresponding pair of reference images of the volume of interest to determine a combined similarity measure between the pair of X-ray images and the corresponding reference images, wherein the combined similarity measure includes six transformation parameters, and wherein the processing device is further configured to search a single combined six-parameter registration search space to maximize the combined similarity measure, wherein the pair of X-ray images is jointly registered with the pair of reference images.

17. The system of claim 16, wherein to search the combined registration search space, the processing device is configured to search for three in-plane translation parameters in two projections, to search for two in-plane rotation parameters in the two projections, and to search for a common out-of-plane rotation parameter in the two projections.

18. A system comprising:
a processing device, wherein the processing device is configured to:
compare a pair of X-ray images of a volume of interest with a corresponding pair of reference images of the volume of interest to determine a combined similarity measure between the pair of X-ray images and the corresponding reference images,
wherein the combined similarity measure includes six transformation parameters; and
search a combined six-parameter registration search space to maximize the combined similarity measure, wherein the pair of X-ray images is jointly registered with the pair of reference images, and wherein a search of the combined six-parameter registration search space includes a search for no more than three in-plane translation parameters in two projections, a search for no more than two in-plane rotation parameters in the two projections, wherein the search for the two out-of-plane rotation parameters in the two projections includes searching initially for the two in-plane rotation parameters using two-parameter multi-resolution matching, and refining the two in-plane rotation parameters using one of 2-D curve-fitting and gradient minimization, and a search for no more than one common out-of-plane rotation parameter in the two projections.

19. The system of claim 18, further comprising: an imaging system coupled with the processing device to generate the pair of X-ray images of the volume of interest; and means for generating a plurality of pairs of reference images from the 3-D scan of the volume of interest, the pairs of reference images comprising nominal in-plane reference images and a plurality of out-of-plane reference images in two projections.

20. The system of claim 18, wherein the combined registration search space comprises a plurality of transformation parameters, and wherein the processing device is further configured to convert the plurality of transformation parameters into a 3-D rigid transformation of the volume.

21. The system of claim 18, wherein to search for the three in-plane translation parameters in the two projections, the processing device is configured to search initially for the three in-plane translation parameters using three-parameter multi-resolution matching, and to refine the three in-plane translation parameters using one of three-parameter sub-pixel matching and three-parameter gradient minimization.

22. The system of claim 18, wherein to search for the common out-of-plane rotation parameter in the two projections, the processing device is configured to search initially for the common out-of-plane rotation parameter using a 1-D search method, and to refine the common out-of-plane rotation parameter using the 1-D search method and interpolation.

23. The system of claim 18, wherein the processing device is further configured to determine whether the plurality of transformation parameters have enough accuracy to achieve a desired registration accuracy, to repeat the method of claim 17 if the plurality of transformation parameters do not have enough accuracy to achieve the desired registration accuracy, else to apply the 3-D rigid transformation to the volume of interest.

24. An apparatus, comprising:
means for comparing a pair of X-ray images of a volume of interest with a corresponding pair of reference images from a 3-D scan of the volume of interest to determine a combined similarity measure between the pair of X-ray images and the corresponding pair of reference images, wherein the combined similarity measure includes six transformation parameters; and
means for searching a single combined six-parameter registration search space to maximize the combined similarity measure, wherein the pair of X-ray images is jointly registered with the pair of reference images.

25. The apparatus of claim 24, wherein the combined registration search space comprises a plurality of transformation parameters, the method further comprising converting the plurality of transformation parameters into a 3-D rigid transformation of the volume.

* * * * *